United States Patent
Sambursky et al.

(10) Patent No.: US 8,669,052 B2
(45) Date of Patent: Mar. 11, 2014

(54) LATERAL FLOW NUCLEIC ACID DETECTOR

(75) Inventors: Robert P. Sambursky, Bradenton, FL (US); Uma Mahesh Babu, Bradenton, FL (US); Robert W. VanDine, Montoursville, PA (US)

(73) Assignee: Rapid Pathogen Screening, Inc., Sarasota, FL (US)

( * ) Notice: Subject to any disclaimer, the term of this patent is extended or adjusted under 35 U.S.C. 154(b) by 282 days.

(21) Appl. No.: 12/502,626

(22) Filed: Jul. 14, 2009

(65) Prior Publication Data

US 2009/0305290 A1 Dec. 10, 2009

Related U.S. Application Data

(63) Continuation-in-part of application No. 12/481,631, filed on Jun. 10, 2009.

(60) Provisional application No. 61/080,879, filed on Jul. 15, 2008, provisional application No. 61/098,935, filed on Sep. 22, 2008, provisional application No. 61/179,059, filed on May 18, 2009, provisional application No. 61/060,258, filed on Jun. 10, 2008.

(51) Int. Cl.
*C12Q 1/68* (2006.01)
*C12M 1/34* (2006.01)
*C12M 3/00* (2006.01)
*G01N 21/00* (2006.01)
*G01N 21/76* (2006.01)
*C12P 19/34* (2006.01)

(52) U.S. Cl.
USPC ... 435/6.1; 435/287.1; 435/287.2; 435/287.7; 436/164; 436/172; 536/23.1; 536/24.3

(58) Field of Classification Search
None
See application file for complete search history.

(56) References Cited

U.S. PATENT DOCUMENTS

| | | | |
|---|---|---|---|
| 4,563,417 | A | 1/1986 | Albarella et al. |
| 4,859,612 | A | 8/1989 | Cole et al. |
| 4,956,302 | A | 9/1990 | Gordon et al. |
| 4,960,691 | A | 10/1990 | Gordon et al. |
| 4,960,692 | A | 10/1990 | Lentrichia et al. |

(Continued)

FOREIGN PATENT DOCUMENTS

| | | |
|---|---|---|
| DE | 19622503 | 7/1998 |
| EP | 0306772 A1 | 3/1989 |

(Continued)

OTHER PUBLICATIONS

GenBank Accession No. AY265708 (Aug. 2004).*

(Continued)

*Primary Examiner* — Teresa E Strzelecka
(74) *Attorney, Agent, or Firm* — Brown & Michaels, PC

(57) ABSTRACT

Point-of-care binding assays include at least one target nucleic acid binding in a multiplex structure with at least one sequence in a partner nucleic acid associated with a label, due to complementary base pairings between at least one sequence in the target nucleic acid and at least one sequence in the partner nucleic acid. The assays overcome the inherent deficiencies of antibody-protein antigen assays. In a preferred embodiment, color tagged nucleic acid sequences are used to bind a complementary target nucleic acid. The tagged nucleic acid sequences are preferably made from deoxyribonucleotides, ribonucleotides, or peptide nucleotides.

19 Claims, 8 Drawing Sheets

(56) References Cited

U.S. PATENT DOCUMENTS

| | | | |
|---|---|---|---|
| 5,120,643 | A | 6/1992 | Ching et al. |
| 5,310,650 | A | 5/1994 | McMahon et al. |
| 5,312,921 | A | 5/1994 | Glazer et al. |
| 5,436,134 | A | 7/1995 | Haugland et al. |
| 5,496,562 | A | 3/1996 | Burgoyne |
| 5,637,469 | A | 6/1997 | Wilding et al. |
| 5,658,751 | A | 8/1997 | Yue et al. |
| 5,695,949 | A | 12/1997 | Galen et al. |
| 5,705,353 | A | 1/1998 | Oh et al. |
| 5,714,341 | A | 2/1998 | Thieme et al. |
| 5,756,126 | A | 5/1998 | Burgoyne |
| 5,763,162 | A | 6/1998 | Glazer et al. |
| 5,783,687 | A | 7/1998 | Glazer et al. |
| 5,807,527 | A | 9/1998 | Burgoyne |
| 5,824,268 | A | 10/1998 | Bernstein et al. |
| 5,863,740 | A | 1/1999 | Kientsch-Engel et al. |
| 5,877,028 | A | 3/1999 | Chandler et al. |
| 5,888,778 | A | 3/1999 | Shuber |
| 5,972,386 | A | 10/1999 | Burgoyne |
| 5,985,327 | A | 11/1999 | Burgoyne |
| 5,989,813 | A | 11/1999 | Gerdes |
| 5,998,220 | A | 12/1999 | Chandler |
| 6,017,767 | A | 1/2000 | Chandler |
| 6,037,127 | A | 3/2000 | Ebersole et al. |
| 6,046,058 | A | 4/2000 | Sun |
| 6,054,272 | A | 4/2000 | Glazer et al. |
| 6,060,237 | A | 5/2000 | Nygren et al. |
| 6,087,184 | A | 7/2000 | Magginetti et al. |
| 6,106,779 | A | 8/2000 | Buechler et al. |
| 6,136,610 | A | 10/2000 | Polito et al. |
| 6,225,046 | B1 | 5/2001 | Vesey et al. |
| 6,277,652 | B1 | 8/2001 | Jo et al. |
| 6,335,205 | B1 | 1/2002 | Bausback |
| 6,350,578 | B1 | 2/2002 | Stark et al. |
| 6,355,429 | B1 | 3/2002 | Nygren et al. |
| 6,358,752 | B1 | 3/2002 | Durst et al. |
| 6,514,773 | B1 | 2/2003 | Klein et al. |
| 6,566,101 | B1 | 5/2003 | Shuber et al. |
| 6,569,627 | B2 | 5/2003 | Wittwer et al. |
| 6,783,938 | B2 | 8/2004 | Nygren et al. |
| 6,875,619 | B2 | 4/2005 | Blackburn |
| 6,902,900 | B2 | 6/2005 | Davies et al. |
| 7,189,522 | B2 | 3/2007 | Esfandiari |
| 7,309,611 | B2 | 12/2007 | DiNello et al. |
| 7,314,763 | B2 | 1/2008 | Song et al. |
| 7,341,837 | B2 | 3/2008 | Lawton |
| 7,371,582 | B2 | 5/2008 | Nahm et al. |
| 7,374,950 | B2 | 5/2008 | Kang et al. |
| 7,393,697 | B2 | 7/2008 | Charlton |
| 7,425,302 | B2 | 9/2008 | Piasio et al. |
| 7,566,573 | B2 | 7/2009 | Carpenter et al. |
| 7,723,124 | B2 | 5/2010 | Aberl et al. |
| 2003/0073121 | A1 | 4/2003 | Mendel-Hartvig et al. |
| 2003/0104506 | A1 | 6/2003 | Durst et al. |
| 2003/0108940 | A1 | 6/2003 | Inoko et al. |
| 2003/0186463 | A1 | 10/2003 | Hudak et al. |
| 2003/0190681 | A1 | 10/2003 | Shai |
| 2004/0053255 | A1 | 3/2004 | Lee et al. |
| 2004/0072176 | A1 | 4/2004 | Lee et al. |
| 2004/0110167 | A1 | 6/2004 | Gerdes et al. |
| 2004/0152142 | A1 | 8/2004 | Klepp et al. |
| 2004/0156037 | A1 | 8/2004 | Mawhirt et al. |
| 2004/0241779 | A1 | 12/2004 | Piasio et al. |
| 2005/0032244 | A1 | 2/2005 | Nie et al. |
| 2005/0164305 | A1 | 7/2005 | Golz et al. |
| 2005/0227223 | A1 | 10/2005 | Miyawaki |
| 2005/0227275 | A1 | 10/2005 | Jung et al. |
| 2005/0239056 | A1 | 10/2005 | Piasio et al. |
| 2006/0003390 | A1 | 1/2006 | Schaffler et al. |
| 2006/0019406 | A1 | 1/2006 | Wei et al. |
| 2006/0057608 | A1 | 3/2006 | Kaufman |
| 2006/0160078 | A1 | 7/2006 | Cardy et al. |
| 2006/0199278 | A1 | 9/2006 | Leclipteux et al. |
| 2006/0223192 | A1 | 10/2006 | Smith et al. |
| 2006/0240569 | A1 | 10/2006 | Goldenbaum et al. |
| 2006/0263907 | A1 | 11/2006 | Zweig |
| 2007/0003992 | A1 | 1/2007 | Pentyala |
| 2007/0015290 | A1 | 1/2007 | Raj |
| 2007/0059682 | A1 | 3/2007 | Aberl et al. |
| 2007/0141564 | A1 | 6/2007 | Aberl et al. |
| 2007/0184506 | A1 | 8/2007 | Klepp |
| 2007/0202497 | A1 | 8/2007 | Renuart et al. |
| 2007/0224701 | A1 | 9/2007 | Rosenstein |
| 2007/0264629 | A1 | 11/2007 | Holmes et al. |
| 2008/0032319 | A1 | 2/2008 | Nam |
| 2008/0085525 | A1 | 4/2008 | Van Herwijnen |
| 2008/0102473 | A1 | 5/2008 | Fouquet et al. |
| 2008/0318341 | A1 | 12/2008 | Esfandiari |
| 2009/0011436 | A1 | 1/2009 | Piasio et al. |
| 2009/0047673 | A1 | 2/2009 | Cary |
| 2009/0155811 | A1 | 6/2009 | Natan et al. |
| 2009/0232702 | A1 | 9/2009 | Wu et al. |
| 2009/0305231 | A1 | 12/2009 | Weidemaier et al. |
| 2010/0143891 | A1 | 6/2010 | Aberl et al. |
| 2010/0143941 | A1 | 6/2010 | Wu et al. |
| 2010/0209297 | A1 | 8/2010 | Raj et al. |
| 2010/0291536 | A1 | 11/2010 | Viljoen et al. |

FOREIGN PATENT DOCUMENTS

| | | | |
|---|---|---|---|
| EP | 1489416 | A1 | 12/2004 |
| GB | 1561042 | | 2/1980 |
| WO | 9416108 | A1 | 7/1994 |
| WO | 9960402 | A1 | 11/1999 |
| WO | 0029112 | A1 | 5/2000 |
| WO | 0204122 | A2 | 1/2002 |
| WO | 03073817 | A2 | 9/2003 |
| WO | 2007063326 | A2 | 6/2007 |
| WO | 2007123507 | A1 | 11/2007 |
| WO | 2008014709 | A1 | 2/2008 |
| WO | 2009044167 | A1 | 4/2009 |

OTHER PUBLICATIONS

Uchio, et al., "Rapid Diagnosis of Adenoviral Conjunctivitis on Conjunctival Swabs by 10-Minute Immunochromatography," Opthalmology, vol. 104, No. 8, Aug. 1997, pp. 1294-1299.

Sambursky et al., "The RPS Adeno Detector for Diagnosing Adenoviral Conjunctivitis", Ophthalmology, vol. 113, No. 10, pp. 1758-1764 (Oct. 2006).

Sambursky, "510-K Summary of Safety and Effectiveness" (Sep. 14, 2005).

Udeh et al., "Cost Effectiveness of a Point-of-Care Test for Adenoviral Conjunctivitis", The American Journal of the Medical Sciences, vol. 336, No. 3, pp. 254-264 (Sep. 2008).

Bruning et al., "A rapid chromatographic strip test for the pen-side diagnosis of rinderpest virus," Journal of Virological Methods 81 (1999) 143-154.

Berezovski, et al., "Cell lysis inside the capillary facilitated by transverse diffusion of laminar flow profiles (TDLFP)," Anal Bioanal Chem (2007) 387:91-96.

O'Mahony, et al., "Integration of Bacteria Capture via Filtration and in Situ Lysis for Recovery of Plasmid DNA under Industry-Compatible Conditions," Biotechnol. Prog. 2007, 23, pp. 895-903.

"FTA Nucleic Acid Collection, Storage and Purification," Whatman website, http://whatman.com/products.aspx?PID=108.

Karle, et al., "Application of FTA-based Technology for Sample Collection, Transport, Purification, and Storage of PCR-ready Plant DNA" (Nov. 2003).

Barnard, et al., "Development of an Oligonucleotide-Based SNP Detection Method on Lateral Flow Strips Using Hexapet Tags," Point of Care, vol. 4, No. 3, pp. 108-118 (Sep. 2005).

Choi, et al., "A rapid, simple measurement of human albumin in whole blood using a fluorescence immunoassay (I)," Clinica Chimica Acta 339 (2004) pp. 147-156.

Parida M M, "Rapid and real-time detection technologies for emerging viruses of biomedical importance," J. Biosci. 33 (4), Nov. 2008, 617-628.

(56) References Cited

OTHER PUBLICATIONS

International Search Report and Written Opinion dated Jan. 22, 2010, International Application No. PCT/US2009/046848.
International Search Report and Written Opinion dated Feb. 18, 2010, International Application No. PCT/US2009/050645.
International Search Report and Written Opinion dated Mar. 12, 2010, International Application No. PCT/US2009/050653.
Chieux V, Hober D, Harvey J, Lion G, Lucidarme D, Forzy G, Duhamel M, Cousin J, Ducoulombier H, Wattre P. The MxA protein levels in whole blood lysates of patients with various viral infections. J Virol Methods. 1998;70:183-191.
Extended European Search Report for EPO Application No. 09798690.5. Issue on Oct. 24, 2012.
Rule et al. "Rapid Method for Visual Identification of Specific DNA Sequences based on DNA-Tagged Liposomes." Clinical Chemistry. vol. 42, No. 8. pp. 1206-1209. 1996.
Carter et al. "Lateral Flow Microarrays: A Novel Platform for Rapid Nucleic Acid Detection Based on Miniaturized Lateral Flow Chromatography" vol. 35, No. 10. 2007, Nucleic Acids Res., e74.
Dineva et al. "Simultaneous Visual Detection of Multiple Viral Amplicons by Dipstick Assay" vol. 43, No. 8. pp. 4015-4021. 2005.
Kalogianni et al. "Dry Regent Dipstick Test Combined with 23S rDNA PCR for Molecular Diagnosis of Bacterial Infection in Arthroplasty" Analytical Biochemistry 361, pp. 169-175, 2007.
Furuta et al. "Quantitative Study of Helicobacter pylori in Gastric Mucus by Competitive PCR Using Synthetic DNA Fragments." J. Clin. Microbiol., vol. 34, No. 10, pp. 2421-2425 1996.

\* cited by examiner 66  64  62

72  70

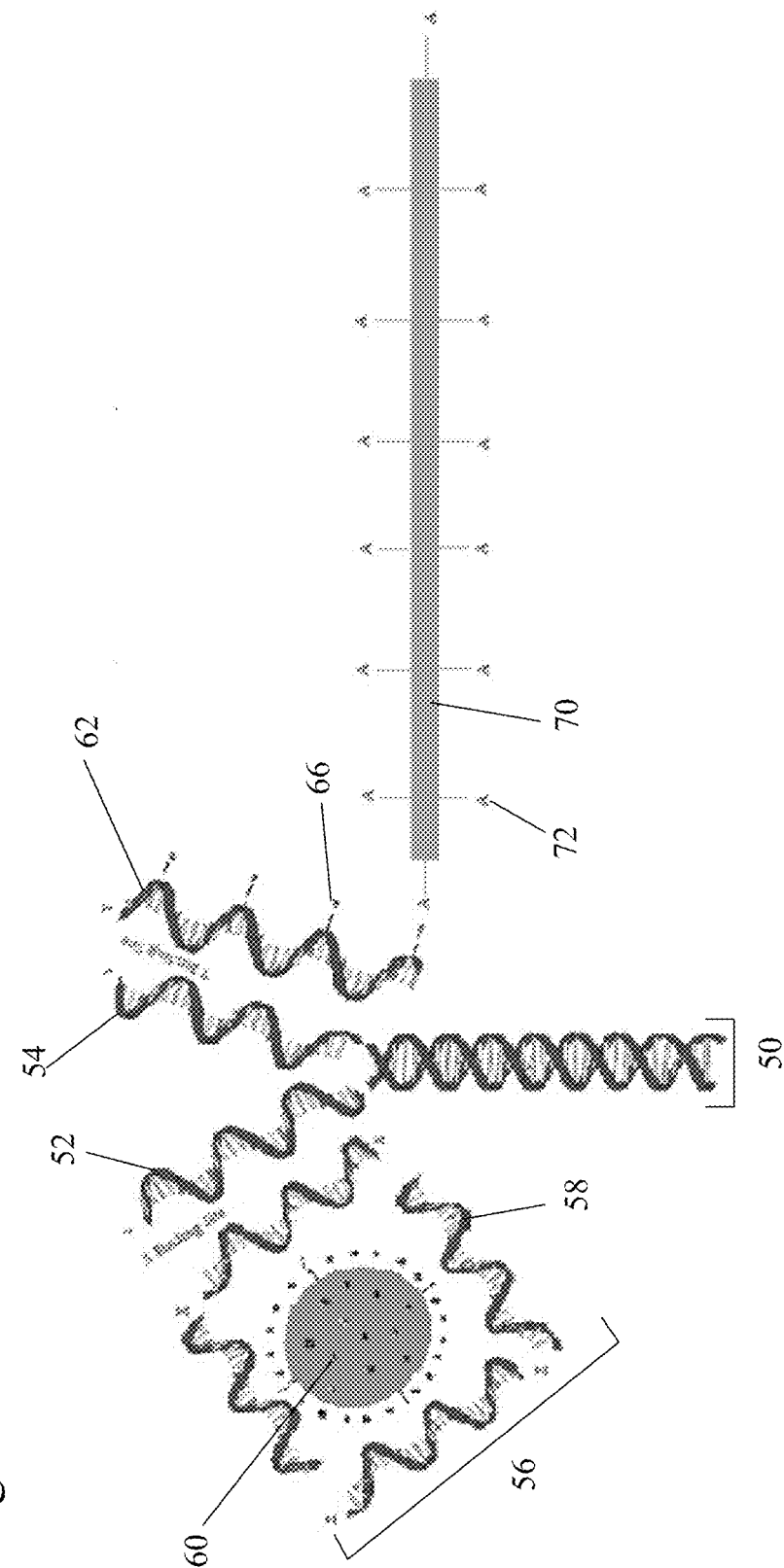

LATERAL FLOW NUCLEIC ACID DETECTOR

REFERENCE TO RELATED APPLICATIONS

This application claims one or more inventions which were disclosed in Provisional Application Ser. No. 61/080,879, filed Jul. 15, 2008, entitled "LATERAL FLOW NUCLEIC ACID DETECTOR", Provisional Application No. 61/098,935, filed Sep. 22, 2008, entitled "IN SITU LYSIS OF CELLS IN LATERAL FLOW IMMUNOASSAYS", and Provisional Application No. 61/179,059, filed May 18, 2009, entitled "METHOD AND DEVICE FOR COMBINED DETECTION OF VIRAL AND BACTERIAL INFECTIONS". The benefit under 35 USC §119(e) of the United States provisional applications are hereby claimed, and the aforementioned applications are hereby incorporated herein by reference.

This application is also a continuation-in-part application of application Ser. No. 12/481,631, filed Jun. 10, 2009, entitled "COMBINED VISUAL/FLUORESCENCE ANALYTE DETECTION TEST", which claimed priority from Provisional Application No. 61/060,258, filed Jun. 10, 2008, entitled "COMBINED VISUAL/FLUORESCENCE ANALYTE DETECTION TEST". The aforementioned applications are hereby incorporated herein by reference.

BACKGROUND OF THE INVENTION

1. Field of the Invention

The invention pertains to the field of nucleic acid detection. More particularly, the invention pertains to a lateral flow assay for detection of nucleic acid targets.

2. Description of Related Art

Lateral flow immunoassays are a subset of antibody-based immunoassays combining various reagents and process steps in one assay strip, thus providing a sensitive and rapid means for the detection of target molecules. Lateral flow immunoassays are available for a wide area of target analytes and can be designed for sandwich or competitive test principles. Generally high molecular weight analytes with several epitopes are analyzed in a sandwich format whereas small molecules representing only one epitope are detected by means of a competitive assay. The first tests were made for human chorionic gonadotropin (hCG). Today, there are commercially available tests for monitoring ovulation, detecting infectious disease organisms, analyzing drugs of abuse, and measuring other analytes important to human physiology. Products have also been introduced for veterinary testing, environmental testing, and product monitoring.

Rapid point-of-care analysis is becoming increasingly important in the diagnosis and treatment of various viral and other pathogenic microbiological agents. Prior art point-of-care tests, such as lateral flow immunochromatography tests, are immunoassays involving an antibody and its antigen. Binding assays in such formats operate on the basis of ligands and receptors and their associated binding constants. The inherent deficiencies in the associations between antibodies and their antigens are well known in the art in that ligand-receptor binding assays are prone to degrade with temperature cycling and heat stress while in storage, and interferences often occur from components in the sample matrix, causing non-specific binding during the assay and leading to false results. These inherent limitations do not provide sufficient specificity in the ligand-receptor interaction for reliable assay results. Ligand-receptor binding provides the above-mentioned specificity and limitations to a protein antigen target but not to a nucleic acid sequence coding for the protein.

SUMMARY OF THE INVENTION

A binding assay of the present invention includes a target nucleic acid binding in a multiplex structure with at least one sequence in another nucleic acid associated with a label, due to complementary base pairings between at least one sequence in the target nucleic acid with at least one sequence in the labeled nucleic acid. The assays of the present invention overcome the inherent deficiencies of antibody-protein antigen assays. In a preferred embodiment, color tagged nucleic acid sequences are used to bind a complementary target nucleic acid. The tagged nucleic acid sequences are preferably made from deoxyribonucleotides, ribonucleotides, or peptide nucleotides.

BRIEF DESCRIPTION OF THE DRAWINGS

FIG. 9 schematically shows the complexes and the target nucleic acid which will be bound to and read at the test line in the second embodiment of the present invention.

DETAILED DESCRIPTION OF THE INVENTION

Figure 1:
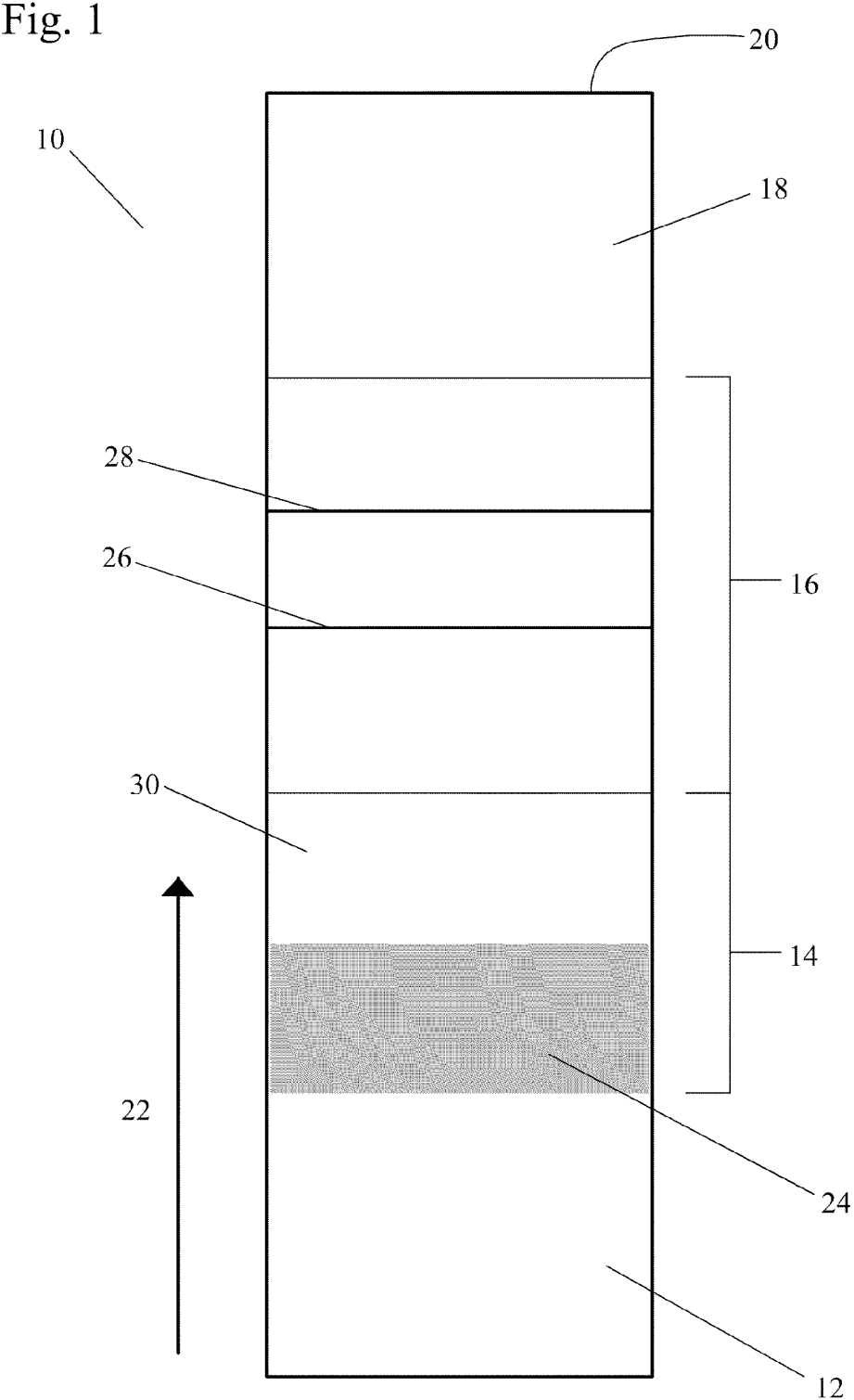
FIG. 1 shows a schematic top view of a test strip for a lateral flow binding assay in an embodiment of the present invention.

A lateral flow nucleic acid detector of the present invention preferably detects nucleic acids in a sample without utilizing the polymerase chain reaction as an amplification step designed to enhance sensitivity for the target nucleic acid. In some embodiments, the detected nucleic acids are also quantified. Some examples of how the nucleic acids may be quantified include, but are not limited to, quantification through visual gradations of the line intensity or through the use of an electronic optical reader.

The assays described herein are preferably "point-of-care assays", which, as defined herein, include both lateral flow assays and flow through assays. These point-of-care assays may be run and read within a matter of minutes to a few hours after the sample is obtained, but the assays may alternatively be run at a later time such as up to 24 to 46 hours after obtaining the sample.

The detector may be used to detect a target nucleic acid sequence associated with any target virus, bacterium, fungus, protozoa, other pathogens, allergens, any genetic deficiency, or any other target nucleic acid in a sample. Other target nucleic acids include, but are not limited to, those that code for tumor markers (oncogenes), cardiac markers (for example, myoglobin, troponin, creatine kinase, MMP-9, C-reactive protein) inflammatory markers (such as cytokines, lymphokines, chemokines, cellular signaling factors, chemoattractants, metalloproteinases, interferons, MxA, and growth factors), hormones, and tissue typing. The target nucleic acid may be any nucleic acid including, but not limited to, DNA, an oligonucleotide, messenger RNA, or any other type of RNA. The flow of the transport liquid in the detector may be gravity-dependent or as a result of capillary action or surface tension. The transport liquid may be applied by dipping the test strip in the transport liquid or the transport liquid may be contained in a test housing for the test strip.

The nucleic acid sequences used to detect the target nucleic acid sequences can be of any length such that they are specific to the target of interest. In preferred embodiments, the sequences are approximately 10 to 25 nucleotides long, however, longer or shorter sequences are possible, as long as they provide the requisite specificity and do not otherwise interfere with the assay. In some preferred embodiments, the sequences are around 15 to 17 nucleotides long. If peptide nucleic acid sequences (PNAs) are being used, the length may be as short as 10 or 11 nucleotides. If PCR primers are being used, they are generally 16 to 24 nucleotides long.

A lateral flow nucleic acid detector of the present invention may be uniplanar with a single sheet on a test strip for the detection zone. Alternatively, the detector may be multiplanar with multiple detection zones on multiple sheets in fluid communication for simultaneous assays for the same or different target nucleic acids from the same or different samples.

A sample for testing in the present invention may be any sample expected to potentially include a target nucleic acid including, but not limited to, saliva, nasopharyngeal secretions, mucus, tissue, blood, urine, tears, vaginal fluid, skin ulcerations, an environmental water sample, and a soil sample. In most cases, it is preferable to add a denaturant or lysis agent in situ to the sample in order to make the nucleic acids in the sample accessible to the first and second complexes. Although the denaturant or lysis agent may be added to the sample prior to application of the sample to the test strip, the denaturant or lysis agent is preferably pre-loaded onto a zone of the test strip as a dried denaturant or lysis agent so that the sample may be applied directly to the test strip without a step of adding denaturant or lysis agent. Alternatively, the lysis agent may be pre-dried by freeze drying or lyophilizing and then pre-loaded into the test strip. The lysis agent can be absorbed, adsorbed, embedded, or trapped on the test strip. The dried or embedded denaturant or lysis agent is pre-loaded onto the test strip in a location so that it frees the nucleic acids prior to the sample reaching the first complex on the test strip. The dried or embedded denaturant or lysis agent is preferably soluble in the transport liquid and located in the sample application zone or between the sample application zone and the zone where the first complex is pre-loaded. In other embodiments, mild lysis agents may be part of the running buffer. In this scenario, there is no adverse effect on the conjugate zone (the first complex application zone) which will be downstream and the sample may either be upstream or downstream to the conjugate zone.

If the sample that has been collected is not lysed prior to collection and transfer to the sample analysis device, the number of steps needed to collect and prepare the sample for analysis is decreased. In these embodiments, following sample loading, the sample traveling with the transport liquid (buffer) will encounter a lysis agent. The lysis agent will have preferably been pre-loaded and dried onto the test strip and is eluted by the transport liquid. The initially dried lysis agent is preferably localized between the sample application zone and a conjugate zone (the first complex application zone) or overlapping either or both of these zones. The lysis agent is preferably soluble in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the analyte, including any lysis-freed components, to a detection zone.

The location where the lysis agent is pre-loaded and dried (or embedded) can be varied as needed. In order to maximize the time that the sample has to interact with the lysis agent as well as to minimize the amount of lysis agent reaching the detection zone, the lysis agent may be located in or just downstream of the sample application zone. Alternatively, in order to minimize the distance along which the lysis product must travel before reaching the conjugate zone, the lysis agent may be located closer to the conjugate zone (the first complex application zone).

In one embodiment, the sensitivity of visually read nucleic acid assay tests is enhanced by adding a small quantity of fluorescing dye or fluorescing latex bead conjugates to the initial conjugate material. When the visible spectrum test line is visibly present, the test result is observed and recorded. However, in the case of weak positives that do not give rise to a distinct visual test line, a light of an appropriate spectrum, such as a UV spectrum, is cast on the test line to excite and fluorescent the fluorescing latex beads which are bound in the test line to enhance the visible color at the test line.

Lateral flow devices are known, and are described in, e.g., U.S. Published Patent Application Nos. 2005/0175992 and 2007/0059682. The contents of both of these applications are incorporated herein by reference. Other lateral flow devices known in the art could alternatively be used with the systems and methods of the present invention.

U.S. Published Patent Application No. 2007/0059682 discloses detecting an analyte and a sample which can also contain one or more interfering substances. This publication teaches separating the analyte from the interfering substances by capturing the interfering substances on the chromatographic carrier, and detecting the analyte on the carrier separated from the interfering substances.

U.S. Published Patent Application No. 2005/0175992 discloses a method for detecting targets, such as pathogens and/or allergy-associated components, in a human body fluid where the body fluid sample is collected by a collection device, such as a swab member. The samples are transferred from the swab member to a sample analysis device, on which an analysis of the targets can occur by immunochemical or enzymatic means. The test result is capable of being displayed within a very short period of time and can be directly read by the user. This enables point-of-care testing with results available during a patient visit. The inventions disclosed in this copending application are particularly advantageous for the diagnosis of conjunctivitis.

FIG. 1 shows a schematic top view of a test strip for a lateral flow binding assay for nucleic acid detection in an embodiment of the present invention. While the test strip shown in FIG. 1 has a certain configuration, other configurations with different locations for sample application, first and second complex loading, and placement of the denaturant/lysis agent are within the spirit of the present invention. The test strip 10 in this example includes a first section 12, a second section 14, a third section 16, and optionally a fourth section 18. These sections are preferably mounted on a backing material 20. Flow occurs in the upward direction 22 of FIG. 1. The fourth section 18 serves as an optional waste pad for collecting the transport liquid and materials flowing past the third section 16, also termed the detection zone herein, which preferably includes a nitrocellulose membrane. A first complex, as described below, is loaded onto a conjugate zone, which is the lower portion 24 of the second section 14 in this figure. In one embodiment, a second complex, as described below, is loaded onto a test zone 26 of the detection zone 16. In another embodiment, the second complex is loaded onto the upper portion 30 of the second section 14. In this embodiment, the second complex includes an immobilization agent, such as biotin, and the test zone 26 has an immobilization site, such as an avidin, neutrAvidin, or streptavidin functionality for binding the second complex to the test zone 26. A third complex, as described below, is preferably loaded onto a control zone 28 of the detection zone 16 above the test zone 26. The test zone 26 and control zone 28 are preferably zones with lengths much greater than their widths on the detection zone 16.

In one embodiment of the present invention, the target nucleic acid in the sample to be tested moves faster than the first complex in the transport liquid. In this embodiment, the sample is loaded onto the first section 12 below the first complex and a transport liquid, such as a running buffer, is applied to the first section 12 below where the sample is loaded to perform the assay. Alternatively, the sample solution itself may be used as the transport liquid in this embodiment. In another embodiment, the target nucleic acid in the sample to be tested moves slower than the first complex in the transport liquid. In this embodiment, the sample is loaded onto the upper portion 30 of the second section 14 and the transport liquid is applied to the first section 12 of the test strip. In both embodiments, the assay is preferably run until substantially all the first complex which has not bound to the test line 26 reaches the control line 28. Note that the location of sample loading and first complex loading depends on the conditions of the assay, and may be varied as long as the sample encounters the first complex on the test strip such that the target nucleic acid sequence can bind to the complementary nucleic acid sequence on the labeled first complex. For example, the sample may be added directly onto the first complex (the conjugate) and other embedded materials or slightly downstream or slightly upstream from the first complex and the embedded materials.

In an embodiment of the present invention, at least one first nucleic acid sequence is conjugated to a label to form the first complex. The term "label" as used herein refers to any atom, atoms, molecule, or molecules, such as a fluorescent tag, attached to or associated with a nucleic acid and used to provide a detectable and preferably quantifiable signal. The nucleic acid sequence may be suitably associated with the label through a non-covalent association such as biotin-avidin. Similarly, the label may be microbeads such as colloidal gold particles mixed with fluorescence or fluorescent beads, or dyed latex beads, where the dye may be a visual dye such as a red dye, a fluorescent dye, a phosphorescent dye, or a chemiluminescent dye. These first complexes are used in the mobile phase of the lateral flow chromatography. Methods of detection of the label include, but are not limited to, fluorescence, chemoluminescence, radioactivity, colorimetry, gravimetry, X-ray diffraction, X-ray absorption, magnetism, and enzymatic activity. Visible spectrum test lines may be interpreted by a spectrometer to yield quantified test results. The first complex is placed on the lateral flow strip in a form such that the first complex is mobilized by a transport liquid such as a running buffer or by a sample applied to the lateral flow strip.

Qualitative interpretation is performed visually by observing the test line intensity and hue. In an example where a visual red dye is used as the label, when the concentration of the analyte is equal or slightly above the lower limit of detection, the test line can be seen faintly and the hue is pink. As the concentration of the analyte is increased, the test line intensity correspondingly increases and the hue shifts from pink to bright red. A quantitative interpretation is developed using a spectrometer operating in the visible spectrum. Either an absorption or a reflectance measurement may be used in the visible spectrum to develop the quantification of the test line. First a set of characterized concentrations of the analyte are developed. Each of the concentrations are applied to the sample application zone and the test is developed. The spectrometer is used to measure either the absorbtion or the reflectance of the test line. A standard curve is calculated from the measured values of the spectrometer. The standard curve is normally linear. In other embodiments, if fluorescent tags are used, a similar set of known concentrations of the analyte may be developed. An unknown concentration of the analyte tested and quantified by the spectrometer yields a value that, when plotted on the standard curve, can be correlated to a concentration of analyte.

In one embodiment, a second nucleic acid sequence is immobilized in a second complex on the lateral flow test strip in the test zone. The second nucleic acid sequence may be immobilized by a variety of ways to form the second complex within the spirit of the present invention. The immobilization may be direct, where the immobilization is achieved by binding the nucleic acid sequence to at least one chemical, or indirect, where the immobilization is achieved by physically trapping the nucleic acid sequence with at least one chemical or other moiety. Immobilization methods include, but are not limited to, associating with poly-lysine, coupling to microbeads, and incorporating into a hydrogel. The microbeads, such as latex beads, may be immobilized directly or trapped in the pores of a medium such as a nitrocellulose membrane, a nylon, or a polyester. The hydrogel may be immobilized in a suitable medium directly or by a trapping mechanism.

In one embodiment, different portions of a single continuous sequence of the target nucleic acid could be complementary to both the first nucleic acid sequence and the second nucleic acid sequence. As an example, a peptide nucleic acid sequence (PNAs) of 25 nucleotides is complementary to a portion of a target nucleic acid. Approximately half of those nucleotides (e.g. eleven or twelve nucleotides) are used as the first nucleic acid sequence in the first complex and the other half of the nucleotides (e.g. twelve or thirteen nucleotides) are used as the second nucleotide acid sequence in the second complex. In this example, the first nucleic acid sequence binds to one portion of the single sequence of the target nucleic acid and the second nucleic acid sequence binds to a second portion of the single sequence of the target nucleic acid.

In another embodiment, the second nucleic acid sequence is associated with an immobilization agent to form a second complex. In this embodiment, the second complex is loaded onto the upper portion 30 of the second section 14 of the test strip. A receptor for the immobilization agent is immobilized at an immobilization site on the test zone 26. When the immobilization agent reaches the test zone during the assay, it binds to the receptor to immobilize the second complex on the test zone 26. The immobilization agent and the receptor may be any pair with a strong specific interaction which does not interfere with the desired nucleic acid interactions of the assay. The immobilization agent may be biotin and the receptor may be avidin, neutrAvidin, or streptavidin. Alternatively, the immobilization agent may be a lectin and the immobilization site may be a glycosyl moiety. For example, in some embodiments, the lectin is the Garden pea Lectin and the glycosyl moiety is an erythrocyte glycosyl unit. The immobilization agent and the immobilization site may be reversed within the spirit of the present invention. For example, avidin may be complexed with the second nucleic acid sequence to form the second complex, with biotin acting as the receptor at the immobilization site at the test zone 26.

In a preferred embodiment of the assay, a third nucleic acid sequence complementary to the first nucleic acid sequence is immobilized in a third complex on the control zone. The third nucleic acid may be immobilized by any of the variety of ways discussed above with respect to the second nucleic acid sequence within the spirit of the present invention. The third complex is designed such that in the running of an assay, any of the first complex, which does not bind to the target nucleic acid in the sample, passes the test zone and binds to the third complex when it reaches the control zone. In this way, any of the first complex not bound to the target nucleic acid is detected, and in some embodiments, quantified. Although an assay of the present invention may be run without a control zone, a control zone is preferred for confirming negative test results and for comparison to the test zone for positive test results.

The target nucleic acid may be any nucleic acid sequence including, but not limited to, a nucleic acid sequence from a virus, a bacterium, a fungus, a plant, an animal, an artificially produced sequence, a genetically modified organism (GMO), or a fossilized specimen. The sample is applied to the strip in a sample application zone. The sample application zone may precede the first complex, overlap the first complex, or follow the first complex on the test strip. When the sample is applied following the first complex, a transport liquid is used to mobilize the first complex and transport the first complex to expose it to any of the target nucleic acid the sample.

In one embodiment, the test zone is composed of at least one immobilized nucleic acid sequence that is a sequence used in traditional polymerase chain reaction (PCR) assays. The sequence is preferably made from deoxyribonucleotides, ribonucleotides, or peptide nucleotides. In this embodiment, the first complex includes such a PCR-type primer of the target nucleic acid conjugated to a label. These primers are preferably the anti-sense nucleotide sequences that complement their corresponding "sense" sequences of nucleic acid from organisms such as viruses, bacteria, and fungi. The sense and anti-sense primers may be interchanged in the lateral flow assay within the spirit of the present invention.

Although only one test line is shown in the figures, multiple test lines are within the spirit of the invention. In some embodiments where there are multiple targets, the presence of each target preferably corresponds to a separate test line. In other embodiments where there are multiple targets, the presence of multiple targets may be indicated on the same test line such that the presence of more than one target has different characteristics than the presence of a single target. For example, the presence of multiple targets on the same test line may be visually indicated by a different color than the presence of each of the targets alone.

Figure 2:
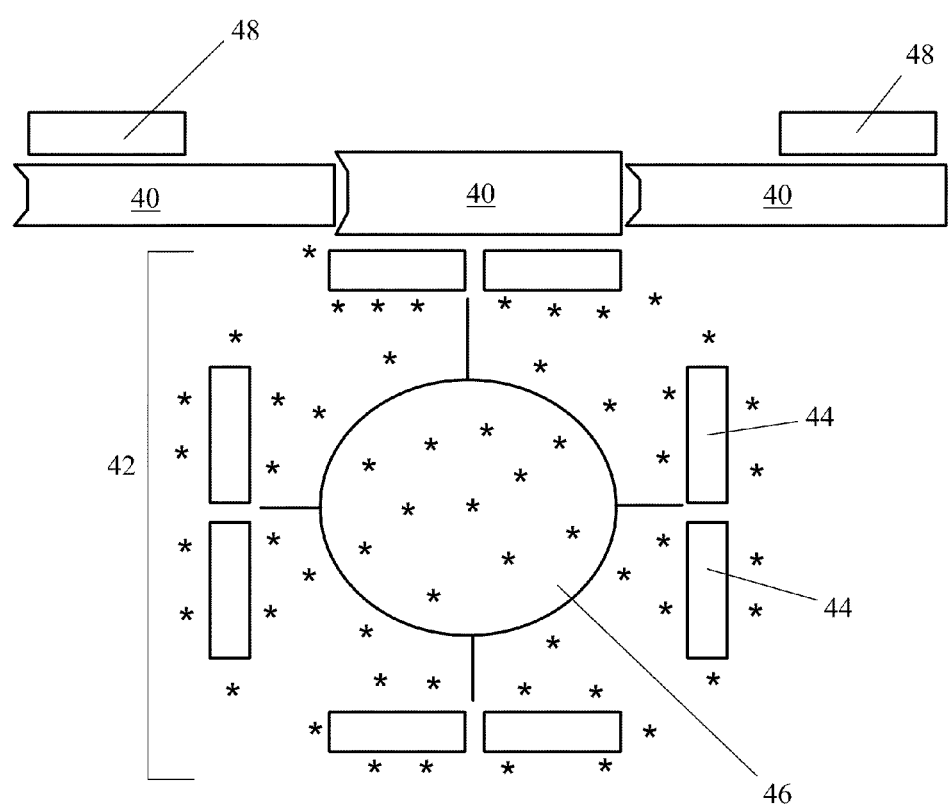
FIG. 2 schematically shows a positively-detectable complex of a single-stranded target nucleic acid in a first embodiment of the present invention.

FIG. 2 shows a positively-detectable complex of a target nucleic acid in a first embodiment of the present invention. In this embodiment, the target nucleic acid 40 in the sample is a single-stranded nucleic acid sequence. The first complex 42 includes at least one first nucleic acid sequence 44 complementary to an inner part of the sequence of the target nucleic acid 40. The first nucleic acid sequence 44 is associated with a label 46. The second complex includes at least one second nucleic acid sequence 48 complementary to an outer part of the sequence of the target nucleic acid 40. The use of two sequences complementary to different parts of the target nucleic acid in the lateral flow assay improves the specificity of the assay.

In some embodiments, the first nucleic acid sequence 44 is preferably an inner PCR primer and the second nucleic acid sequence 48 is preferably an outer PCR primer. Alternatively, the first nucleic acid sequence 44 is an outer PCR primer and the second nucleic acid sequence 48 is an inner PCR primer. Although one first nucleic acid sequence and one label is sufficient for each first complex, a first complex preferably has multiple copies of the first nucleic acid sequence, as shown in FIG. 2, and multiple label units, shown as asterisks in FIG. 2. Although eight nucleic acid sequences are shown in FIG. 2, any number which promotes binding of the first complex to the target nucleic acid may be used within the spirit of the present invention.

Figure 3:
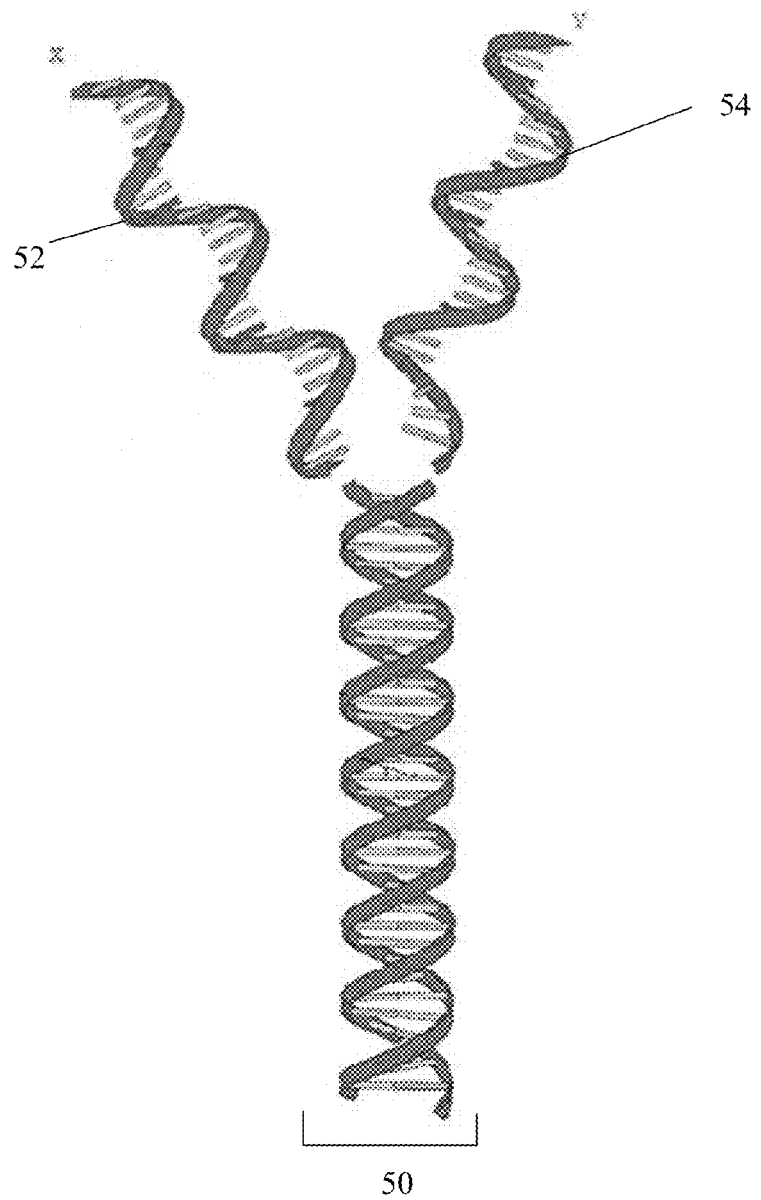
FIG. 3 schematically shows a double-stranded target nucleic acid in a second embodiment of the present invention.

FIGS. 3 through 9 show a positively-detectable complex of a target nucleic acid in a second embodiment of the present invention. As shown in FIG. 3, in this embodiment, the target nucleic acid 50 in the sample is a double-stranded nucleic acid. The target nucleic acid 50 in the sample is preferably denatured in situ, preferably by a denaturant or lysis agent such as DNAzole Direct, formamide, or urea, to open up at least a portion of the double strand to a first strand 52 and a second strand 54. This may be done by adding the denaturant or lysis agent to the sample solution prior to application of the sample to the test strip or the denaturant or lysis agent may be pre-loaded to a zone of the test strip, as discussed earlier. Alternatively, denaturing of the nucleic acid may be achieved by adjusting or controlling the tonicity, the temperature, or the pH of the assay within the spirit of the present invention. A partial opening is preferred for detection in the lateral flow assay, although an assay of the present invention may be run with either partial or complete denaturing of the nucleic acid in the sample.

In a preferred embodiment, the denaturant or lysis agent is located in the sample application zone such that the nucleic acid is denatured and/or lysed soon after it is added to the test strip. In other embodiments, the denaturant or lysis agent is placed on any location on the test strip such that the target nucleic acid is at least partially denatured and/or lysed prior to or while encountering the first labeled complex 56.

Figure 4:
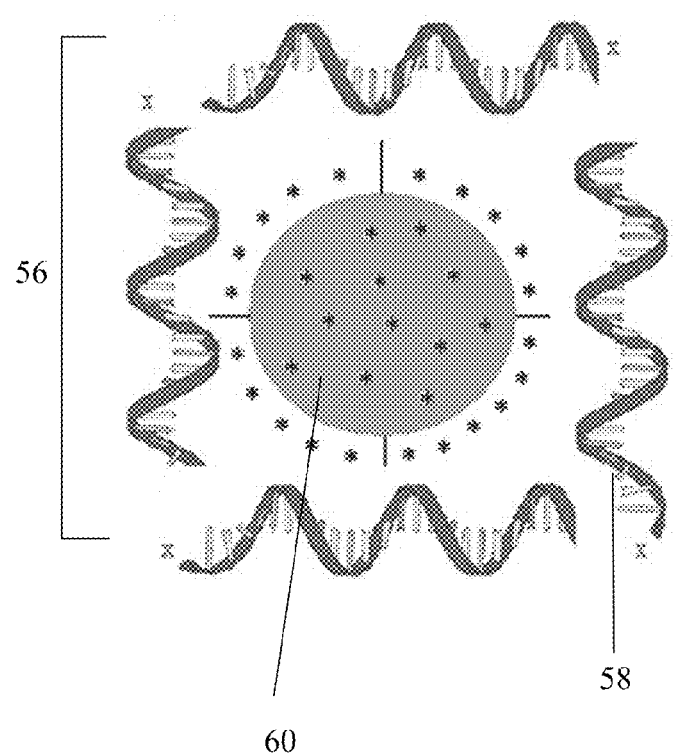
FIG. 4 schematically shows a first labeled complex including a nucleic acid sequence that is complementary to an X-binding site of the target nucleic acid shown in FIG. 3 in a second embodiment of the present invention.

As shown in FIG. 4, the first complex 56 includes at least one first nucleic acid sequence 58, which is preferably a primer or oligonucleotide anti-sense sequence 58 to the first strand 52 of the target nucleic acid sequence. The first nucleic acid sequence 58 is associated with a label 60. The label may be any atom, atoms, molecule, or molecules, such as a visual or fluorescent tag, attached to or associated with a nucleic acid and used to provide a detectable and preferably quantifiable signal. The nucleic acid sequence may be suitably associated with the label through a non-covalent association such as biotin-avidin. Similarly, the label may be microbeads such as colloidal gold particles mixed with fluorescence or fluorescent beads, or dyed latex beads, where the dye may be a visual dye such as a red dye, a fluorescent dye, a phosphorescent dye, or a chemiluminescent dye.

Figure 5:
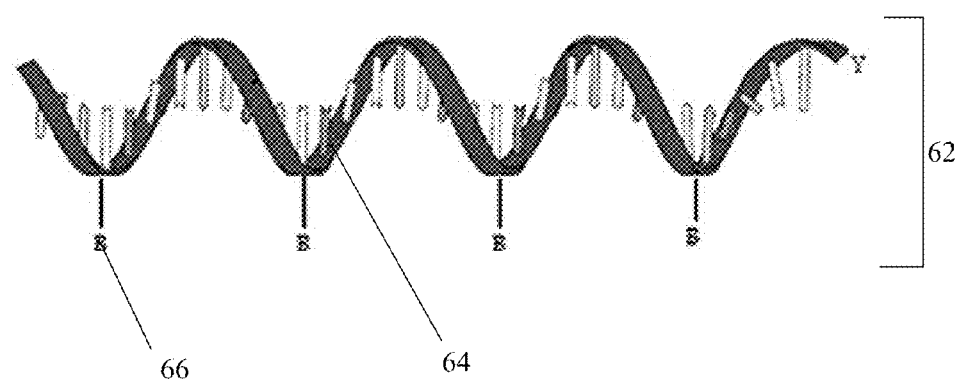
FIG. 5 schematically shows a second complex including a nucleic acid sequence that is complementary to a Y-binding site of the target nucleic acid shown in FIG. 3 in a second embodiment of the present invention.
Figure 6:
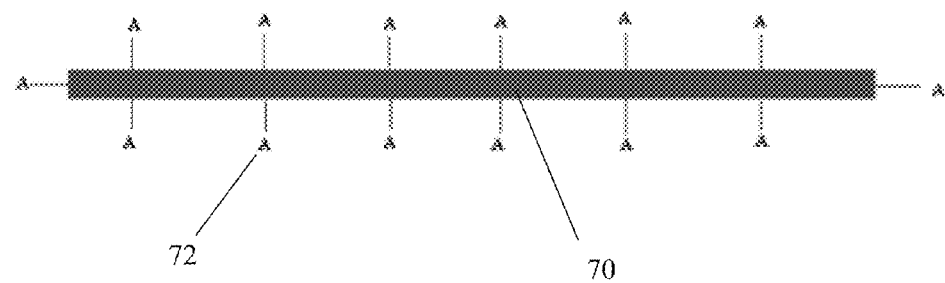
FIG. 6 schematically shows a third complex in a second embodiment of the present invention.

FIG. 5 shows the second complex 62, which includes at least one second nucleic acid sequence 64, which is preferably an anti-sense primer or oligonucleotide, and an immobilization agent 66, such as biotin. The second nucleic acid sequence 64 is complementary to a Y-binding site of the second strand 54 of the target nucleic acid 50. In this embodiment, the second complex 62 is preferably located on the upper portion 30 of the second section 14 of the test strip 10 shown in FIG. 1, and a receptor, such as an avidin-linked probe 70 shown in FIG. 6, is immobilized on the test zone 26 (preferably a nitrocellulose membrane) of the test strip 10 at the start of the assay. The second complex could alternatively be impregnated on the portion of the test strip upon which the sample is loaded or in any location in which it will encounter the sample before the sample reaches the detection zone. In addition, the second complex does not necessarily need to be located downstream of the first complex. For example, a sample pad may be impregnated with biotinylated (B) viral primers or oligonucleotides anti-sense to the single stranded Y DNA of the sample. Although avidin 72 and biotin 66 are shown as the immobilization agents in these figures, other immobilization agents as discussed herein or otherwise known in the art could alternatively be used.

Figure 7:
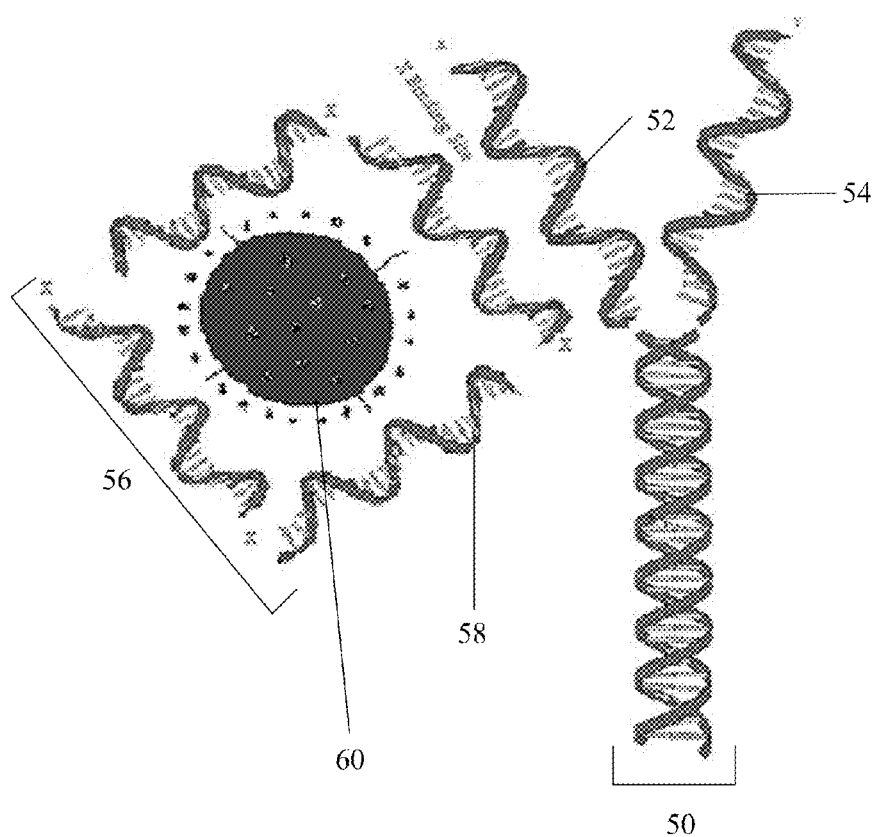
FIG. 7 schematically shows the first complex bound to the X-binding site of the target nucleic acid in the second embodiment of the present invention.

In the embodiment of FIGS. 3 through 9, when the lateral flow is initiated by dipping the absorbent tip in the transport liquid, the first complex 56 is mobilized, and the primer or the oligonucleotide sequence 58 on the first complex 56 complexes with the first strand 52 of the opened nucleic acid at an X-binding site, as shown in FIG. 7. The first complex 56 and the sample nucleic acid 50 may be located anywhere on the test strip such that they encounter each other while being eluted through the test strip.

Figure 8:
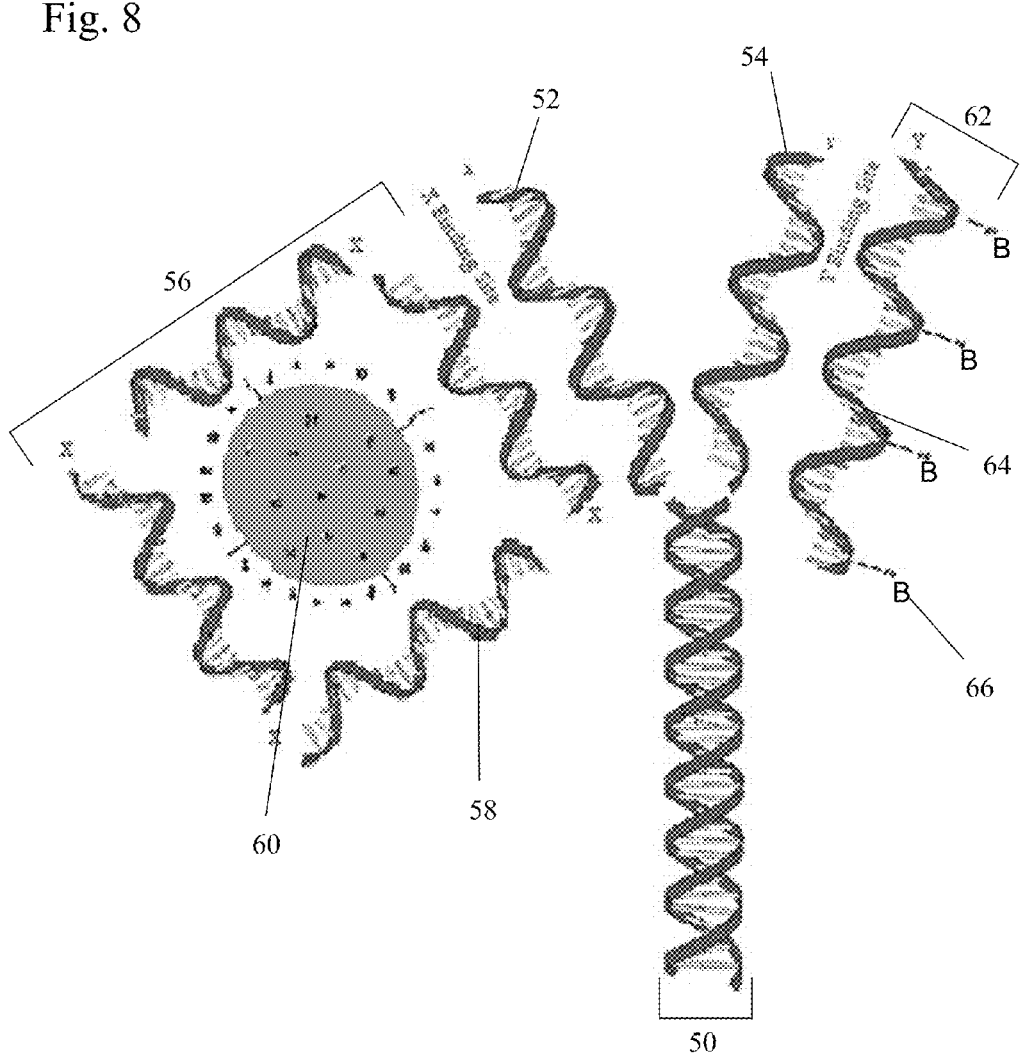
FIG. 8 schematically shows the first complex bound to the X-binding site of the target nucleic acid and the second complex bound to the Y-binding site of the target nucleic acid in the second embodiment of the present invention.

The first-complex-target-nucleic-acid is then exposed to the second complex 62. The second sequence 64 complexes with the second strand 54 at a Y-binding site as shown in FIG. 8. The entire complex shown in FIG. 8 then moves to the test zone, where the biotin 66 is captured by avidin 72 immobilized in the test zone through the binding of the biotin 66 to the avidin 72. This produces a visibly read line. The test zone becomes visible only when the target nucleic acid sequence is present in the sample, indicating that the sample is positive for the target nucleic acid. In a negative sample, where the target nucleic acid sequence is absent, the test zone remains colorless. The intensity of the test zone may be augmented by fluorescence either associated with the visually tagged conjugate particles or mixed with fluorescent conjugate particles. The X-binding site and Y-binding site are preferably non-overlapping sequences, since the first and second nucleic acid sequences are preferably both complementary anti-sense sequences of the target nucleic acid. When the first and second nucleic acid sequences are anti-sense primers, the quality of the engineered primers is important to prevent any potential direct binding between the first sequence and the second sequence in the absence of the target nucleic acid, which would give a false positive test result.

In another embodiment of the present invention, the lateral flow assay tests for more than one target nucleic acid in a sample. In this embodiment, a separate set of first complexes and second complexes are used for each target nucleic acid to be detected. In this embodiment, each first complex has a different label detectable by a different method so that each target nucleic acid may be separately detected and quantified without interference from the other target nucleic acids.

The analytical tests discussed herein preferably permit a result while the patient is still being examined by the practitioner. In a preferred embodiment, the test result is obtained in under 10 minutes after applying the sample to the device, and it is preferably read at approximately 10 minutes. In samples that are highly positive, a readout of the test zone (preferably a test line) is visible within 1 to 5 minutes.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A test strip for detection of at least one target double stranded nucleic acid in a sample comprising:
   at least one detection zone comprising at least one test zone;
   a sample application zone for applying the sample to the test strip;
   a lysis zone comprising at least one lysis or denaturing agent that partially opens the target double stranded nucleic acid into a first single strand and a second single strand;
   at least one first complex comprising at least one first nucleic acid sequence associated with at least one label, wherein the first complex is loaded in a first complex application zone, and wherein the first nucleic acid sequence comprises a sequence complementary to a portion of a sequence of the first single strand of the target nucleic acid; and
   at least one second complex comprising at least one second nucleic acid sequence associated with at least one immobilization agent, wherein the immobilization agent is immobilizable in a test zone of the test strip and wherein the second nucleic acid sequence comprises a sequence complementary to a portion of a sequence of the second single strand of the target nucleic acid;
   wherein the sample, the first complex, and the second complex are all loaded on the test strip at locations such that the sample encounters the lysis zone, and both the first complex and the second complex while running an assay to detect the target nucleic acid in the sample.

2. The test strip of claim 1, wherein the detection zone further comprises a control zone located beyond the test zone for immobilizing any portion of the first complex that does not bind to the target nucleic acid.

3. The test strip of claim 1, further comprising a receptor that recognizes and immobilizes the immobilizing agent, wherein the second complex is loaded at a location upstream of the test zone and the immobilization site is located at the test zone.

4. The test strip of claim 1, further comprising a receptor that recognizes and immobilizes the immobilizing agent, wherein the second complex is loaded at the test zone and the receptor is loaded at a location upstream of the test zone.

5. The test strip of claim 1, wherein the label is selected from the group consisting of:
   a) at least one colloidal gold particle mixed with at least one fluorescent microbead; and
   b) at least one dyed latex microbead.

6. A test strip for detection of at least one target double stranded nucleic acid in a sample comprising:
   at least one detection zone comprising at least one test zone;
   a sample application zone for applying the sample to the test strip;
   a lysis zone comprising at least one lysis or denaturing agent that partially opens the target double stranded nucleic acid into a first single strand and a second single strand;

at least one first complex comprising at least one first nucleic acid sequence associated with at least one label, wherein the first complex is loaded in a first complex application zone, and wherein the first nucleic acid sequence comprises a sequence complementary to a portion of a sequence of the first single strand of the target nucleic acid; and at least one second complex comprising at least one second nucleic acid sequence associated with at least one immobilization agent, wherein the second complex is not immobilized in a test zone at the start of an assay and wherein the immobilization agent is immobilizable in the test zone of the assay, and wherein the second nucleic acid sequence comprises a sequence complementary to a portion of a sequence of the second single strand of the target nucleic acid; and wherein the sample, the first complex, and the second complex are all loaded on the test strip at locations such that the sample encounters the lysis zone, and both the first complex and the second complex while running the assay to detect the target nucleic acid in the sample.

7. The test strip of claim 6, wherein the sample is run on the assay without an amplification step.

8. The test strip of claim 6 further comprising a receptor that recognizes and immobilizes the immobilizing agent at an immobilization site, wherein the second complex is loaded at a location upstream of the test zone and the immobilization site is located at the test zone.

9. The test strip of claim 6, wherein the label is selected from the group consisting of:
a) at least one colloidal gold particle mixed with at least one fluorescent microbead; and
b) at least one dyed latex microbead.

10. The test strip of claim 6, wherein the lysis zone is located in the sample application zone.

11. The test strip of claim 1, wherein the first nucleic acid sequence is a primer or oligonucleotide anti-sense sequence to the first single strand of the target nucleic acid sequence.

12. The test strip of claim 1, wherein the second nucleic acid sequence is a primer or oligonucleotide anti-sense sequence to the second single strand of the target nucleic acid sequence.

13. The test strip of claim 1, wherein the first nucleic acid sequence and the second nucleic acid sequence are non-overlapping sequences.

14. The test strip of claim 6, wherein the first nucleic acid sequence is a primer or oligonucleotide anti-sense sequence to the first single strand of the target nucleic acid sequence.

15. The test strip of claim 6, wherein the second nucleic acid sequence is a primer or oligonucleotide anti-sense sequence to the second single strand of the target nucleic acid sequence.

16. The test strip of claim 6, wherein the first nucleic acid sequence and the second nucleic acid sequence are non-overlapping sequences.

17. A test strip for detection of at least one target double stranded nucleic acid in a sample comprising:
at least one detection zone comprising at least one test zone;
a sample application zone for applying the sample to the test strip;
at least one assay condition that partially opens the target double stranded nucleic acid into a first single strand and a second single strand;
at least one first complex comprising at least one first nucleic acid sequence associated with at least one label, wherein the first complex is loaded in a first complex application zone, and wherein the first nucleic acid sequence comprises a sequence complementary to a first portion of a sequence of the first single strand of the target nucleic acid; and
at least one second complex comprising at least one second nucleic acid sequence associated with at least one immobilization agent, wherein the second complex is not immobilized in a test zone at the start of an assay and wherein the immobilization agent is immobilizable in the test zone of the assay, and wherein the second nucleic acid sequence comprises a sequence complementary to a second portion of a the sequence of the second single strand of the target nucleic acid; and
wherein the sample, the first complex, and the second complex are all loaded on the test strip at locations such that the sample encounters both the first complex and the second complex while running the an assay to detect the target nucleic acid in the sample.

18. The test strip of claim 17, wherein the assay condition is selected from the group consisting of:
a) a tonicity that partially opens the target double stranded nucleic acid;
b) a temperature that partially opens the target double stranded nucleic acid;
c) a pH that partially opens the target double stranded nucleic acid;
d) a lysis agent or denaturant that partially opens the target double stranded nucleic acid, wherein the lysis agent is added to the sample before the sample is applied to the test strip; and
e) any combination of a) through d).

19. The test strip of claim 1, wherein the sample is run on the assay without an amplification step to enhance assay sensitivity for the target nucleic acid.

* * * * *

UNITED STATES PATENT AND TRADEMARK OFFICE
CERTIFICATE OF CORRECTION

PATENT NO. : 8,669,052 B2  Page 1 of 1
APPLICATION NO. : 12/502626
DATED : March 11, 2014
INVENTOR(S) : Sambursky et al.

It is certified that error appears in the above-identified patent and that said Letters Patent is hereby corrected as shown below:

In the Claims:

Claim 17 (Column 12, line 28): replace "a the sequence" with "a sequence"

Claim 17 (Column 12, line 33): replace "the an assay" with "the assay"

Signed and Sealed this
First Day of July, 2014

Michelle K. Lee
*Deputy Director of the United States Patent and Trademark Office*